United States Patent [19]

Inbar

[11] Patent Number: 6,096,268
[45] Date of Patent: Aug. 1, 2000

[54] CHROMOGENIC AND TURBIDIMETRIC ASSAY DEVICE

[75] Inventor: Shai Inbar, Brookline, Mass.

[73] Assignee: Dade Behring Inc., Deerfield, Ill.

[21] Appl. No.: 09/183,305

[22] Filed: Oct. 30, 1998

Related U.S. Application Data

[60] Provisional application No. 60/064,147, Oct. 31, 1997.

[51] Int. Cl.[7] .......................... G01N 31/22; G01N 21/64
[52] U.S. Cl. ...................... 422/56; 422/58; 422/82.08; 422/82.09; 436/165
[58] Field of Search ................................. 422/56, 57, 58, 422/82.08, 82.09; 436/169, 170, 172, 165; 356/246; 250/458.1, 461.1, 461.2

[56] References Cited

U.S. PATENT DOCUMENTS

| | | | |
|---|---|---|---|
| 4,258,001 | 3/1981 | Pierce et al. | 422/56 |
| 4,357,363 | 11/1982 | Pierce et al. | 427/2 |
| 4,381,921 | 5/1983 | Pierce et al. | 436/535 |
| 4,495,293 | 1/1985 | Shaffar | 436/172 |
| 4,704,255 | 11/1987 | Jolley | 422/101 |
| 4,743,561 | 5/1988 | Shaffar | 436/501 |
| 4,870,005 | 9/1989 | Akiyoshi et al. | 435/7 |
| 5,051,237 | 9/1991 | Grenner et al. | 422/56 |
| 5,135,716 | 8/1992 | Thakore | 422/56 |
| 5,173,434 | 12/1992 | Morris et al. | 436/172 |
| 5,217,875 | 6/1993 | Karpf et al. | 435/34 |
| 5,266,486 | 11/1993 | Fraatz et al. | 435/287 |
| 5,364,796 | 11/1994 | Blackwood et al. | 436/500 |
| 5,372,784 | 12/1994 | Morris et al. | 422/82.08 |
| 5,372,936 | 12/1994 | Fraatz et al. | 435/34 |
| 5,376,336 | 12/1994 | Lubbers et al. | 422/82.06 |
| 5,478,753 | 12/1995 | Wong et al. | 436/513 |
| 5,605,665 | 2/1997 | Clark et al. | 422/102 |

OTHER PUBLICATIONS

G. Whiteley, et al., A Viral Conjugate Based Enzyme Immunoassay for Antibodies to Rubella Virus, 92nd American Society for Microbiology, May, 1992.

G. Whiteley, CMV Recombinant Protein pXP1.

P. Wong, et al., A Recombinant Protein Based Enzyme Immunoassay for Antibodies to Human Cytomegalovirus, 91st American Society for Microbiology, May, 1991.

P. Wong, et al., Detection of Antibodies to HIV–1 and–2 with a Rapid Peptide–Based Automated Immunoassay, 6th International Conference on Aids, Jun., 1990.

P. Wong, et al., A Recombinant Protein Based Enzyme Immunoassay for IgM Antibodies to Human Cytomegalovirus, 92nd American Society for Microbiology, May, 1992.

Charles Olive, PhD, Immunoassay System, *Journal of Clinical Immunoassay*, vol. 14, No. 2, Summer, 1991.

Izak Bahar, et al., The Effect of Digibind® on OPUS® Digoxin Assay, Poster, *American Association for Clinical Chemistry*, Jul. 1991–Aug. 1991.

Harald Ackermann, et al., A Dry–chemistry, Multilayer Immunoassay Test for Tobramycin, Poster, *American Association for Clinical Chemistry*, Jul. 1991–Aug. 1991.

Izak Bahar, et al., A Rapid, Self–contained Immunoassay for Total T3, Poster, *American Association for Clinical Chemistry*, Jul. 1991–Aug. 1991.

(List continued on next page.)

*Primary Examiner*—Jeffrey Snay
*Attorney, Agent, or Firm*—Cara Z Lowen

[57] ABSTRACT

The present invention relates to a diagnostic assay device comprising a fluorophore element comprising a fluorophore imbedded therein, and a reagent element. The fluorophore element and reagent element have opposed surfaces which are spaced apart throughout a liquid transport zone a distance effective to cause capillary flow of a sample liquid introduced therebetween throughout the liquid transport zone, the opposed surface of the fluorophore element carrying a plurality of projections arranged throughout the surface in the liquid transport zone, each projection being spaced apart from the others in a predetermined pattern and being in contact or virtual contact with the opposed surface of the reagent element.

13 Claims, 2 Drawing Sheets

OTHER PUBLICATIONS

Alma Padilla, et al., The Efficacy of the OPUS T4 and Thyroid Uptake (TU) Assays in Evaluation of Thyroid Status, Poster, *American Association for Clinical Chemistry*, Jul. 1991–Aug. 1991.

P. Freeley, et al., A Novel Automated Test for the Determination of Antibodies to Toxoplasma gondii, *31st Interscience Conference on Antimicrobial Agents and Chemotherapy*, Sep.–Oct., 1991.

I. Kwasnik, et al., Comparison of Two Automated Methods for Measurement of Toxoplasma gondii Antibodies, *92nd American Society for Microbiology*, May, 1992.

J. Miller, et al., Evaluation of Rapid Automated ELISA to Detect Antibodies to Toxoplasma, *92nd American Society for Microbiology*, May, 1992.

H. Ackermann, et al., Dry Chemistry Multilayer Immunoassay Test for Valproic Acid, Poster, *International Congress of Clinical Chemistry*, Jul. 1990.

J. Blackwood, et al., Dry Chemistry Mutlilayer Immunoassay Test for Carbamazepine, Poster, *International Congress of Clinical Chemistry*, Jul. 1990.

P. D'Eon, et al., Dry Chemistry Multilayer Immunoasay Test For Gentamicin, Poster, *International Congress of Clinical Chemistry*, Jul. 1990.

I. Bahar, et al., Rapid Self–contained Immunoassay for Digoxin, Poster, *International Congress of Clinical Chemistry*, Jul. 1990.

P. Freeley, et al., A Novel Enzyme Immunoassay For Antibodies To Human Immunodeficiency Virus Types 1 and 2, Poster, *International Congress of Clinical Chemistry*, Jul. 1990.

J. Havelick, et al., A Rapid Self–contained Immunoassay For Human Chorionic Gonadotropin (hCG), Poster, *International Congress of Clinical Chemistry*, Jul. 1990.

S. Pothier, et al., Rapid Self–contained Immunoassay for Carcinoembryonic Antigen (CEA), Poster, *International Congress of Clinical Chemistry*, Jul. 1990.

Adrian Leek, et al., A Novel Immunoassay for Hepatitis B Surface Antigen, Poster, *American Association for Clinical Chemistry*, Jul. 1991–Aug. 1991.

Gary Fagan, et al., A Rapid, Self–contained Immunoassay for Human Follicle Stimulating Hormone (hFSH), Poster, *American Association for Clinical Chemstry*, Jul. 1991–Aug. 1991.

Jane Cohen, et al., A Rapid Self–contained Immunoassay for Human Follicle Stimulating Hormone (hFSH), Poster, *American Association for Clinical Chemistry*, Jul. 1991–Aug. 1991.

CHROMOGENIC AND TURBIDIMETRIC ASSAY DEVICE

The present application claims the benefit of U.S. Provisional Application Ser. No. 60/064,147 filed on Oct. 31, 1997, which is fully incorporated herein by reference.

FIELD OF THE INVENTION

The present invention relates to a device for determining an analyte in a biological sample of interest. More particularly, the present invention relates to device that reduces sample volume required, provides excellent sensitivity and enables the use of a fluorometer to determine an analyte in a biological sample of interest by measuring the changes in fluorescence in relation to the changes in the light transmittive properties of the sample.

BACKGROUND OF THE INVENTION

Diagnostic assays based upon the absorbance (chromogenic, colorimetric), light scattering (turbidimetric or nephelometric), and emission of analytes in biological systems are known in the art. In each of these assays, an analyte in a biological system of interest is determined, i.e., its concentration in the biological system of interest, by reacting the analyte of the system with specific assay reagents and monitoring the changes in the either the chromogenic, turbidimetric or emissive properties of the reaction medium. These methods measure the change in the optical properties, that is, the transmittive or emissive properties of an assay solution resulting from the presence of a particular ligand in the assay solution.

For example, in a spectrophotometric assay, the analyte in the sample to be determined and a reagent system specific for the analyte, produces a detectable change in the transmittive properties of the assay solution. The transmittive properties change according to the amount of light absorbed or scattered by an assay solution within a particular wavelength band when a beam of light of known intensity is passed through the assay solution.

Colorimetric assays are a type of spectrophotometric assay in which the change in the transmittive properties, e.g., absorbance, of the solution results in a change in the light absorption of the assay solution. The change in the absorption of the assay solution results, directly or indirectly, from the interaction of the analyte to be determined and the reagent system specific for the analyte. The change in absorbance of the assay solution is related to the concentration of the analyte in the assay solution. Colorimetric assays utilize a chromogenic reagent system capable of interacting in an assay solution with the particular ligand of interest.

Turbidimetric or nephelometric assays are other spectrophometric assays that measure the scattering of light by the assay solution rather than the changes in color. Turbidimetric assays determine the amount of light scattered or blocked by particulate matter as light passes through the assay solution. In these assays, the analyte of interest interacts with a reagent system to form a suspension of particles in the assay solution. As a beam of light having a known intensity is passed through an assay solution, the suspension of particles formed by the interaction of the analyte and reagent system scatters the incident light thereby reducing the intensity of the light transmitted through the assay solution. These assays measure the decrease in the intensity of the light transmitted through an assay solution. The decrease is related to the amount of incident light that is scattered or blocked by the suspension of particles and depends upon the number of particles present and the cross-sectional area of such particles.

Nephelometric assays are similar to turbidimetric assays in that the analyte of interest interacts with a reagent system specific for the analyte to form a suspension of particles in the assay solution. Nephelometric assays measure the amount of incident light scattered by the suspension of particles. Unlike a turbidimetric assay wherein the intensity of the light transmitted through the assay solution is measured, in a nephelometric assay the scattered light is measured at an angle to the light incident to the assay solution. Therefore, in a nephelometric assay the change in the transmittive properties refers to the difference in intensities of light incident to the assay solution and light scattered at an angle to the incident light.

Fluorometric assays typically measure a detectable change in the fluorescent properties of the assay solution. The assay medium is excited with monochromatic light of a wavelength within the excitation wavelength band of the fluorescer. The change in the fluorescent properties of the assay solution is delivered by measuring the intensity of the emitted light at a wavelength within the emission wavelength band of the fluorescent molecule. The intensity of the emitted fluorescent light is related to the concentration of the analyte.

Fluorescent assays are based upon the principle that when a fluorophore is irradiated with light of the appropriate wavelength, the fluorescent intensity of the light emitted by a reaction medium is directly proportional to both the concentration of fluorophore in the reaction medium and the intensity of excitation light impinging the medium. Fluorescent analyzers generally relate changes in the fluorescent intensity of the reaction medium to changes in the concentration of emitting moieties in that medium, by holding the intensity of the excitation light constant. Reagents for fluorescent assays are designed so that the concentration of emitting fluorophores in the reaction medium is changed in proportion to the concentration of the analyte in the sample of the medium.

In general, the analytical instruments designed to measure change in the optical properties of the reaction medium are limited to changes in one type of signal, namely, the signal associated with the absorbent, light scattering and fluorescent properties of the medium. For example, an instrument designed for use in a fluorometric assay generally is not applicable for chromogenic or turbidimetric determinations, without extensive modification of the optics of the instrument to accommodate fluorescence. In the event reaction media that absorb or scatter light also exhibits fluorescence, changes in absorption or scattering may be detected by measurement of change in fluorescence in an instrument designed to detect fluorescence, without the capability of directly detecting chromogenic or turbidimetric changes in the media.

U.S. Pat. No. 4,495,293 describes a method for determining a ligand in a sample suspected of containing the ligand, wherein the method comprises combining to form an assay solution: the sample, an effective amount of a fluorescer; and an effective amount of a reagent system which in the presence of the ligand to be determined is capable of providing a change in the transmittive properties of the assay solution within a wavelength band that overlaps the excitation and/or emission wavelength band of the fluorescer; irradiating the assay solution with light having a wavelength within the excitation wavelength band of the fluorescer; and then measuring the intensity of the fluorescence emitted by the assay solution as a measure of the concentration of the ligand in the sample. In these methods, the fluorescer is added to the assay solution and thus, great care must be taken that there will be no chemical or immunological reaction between the fluorescer and any other component of the assay, e.g., the ligand or reagent system. The fluorescer may also be dependent on the pH range of the reaction system.

It would be useful to have a system for measuring chromogenic or turbidimetric changes in an assay solution using a fluorometric system. It would especially be useful to have a fluorometric system where the fluoroscer or fluorophore does not come in contact with the reagent system.

U.S. Pat. No. 5,173,434 to Morris et al. describes a process to detect or determine the concentration of a substance that directly or indirectly functions to change the light transmissive characteristics of a solution. The method involves providing a light beam forming a transmission light path; providing a solution including said substance in said light path; the improvement comprising positioning a fluorophore, in a chemically inert light transparent matrix, to intersect said light path; and detecting the change in fluorophore emission to determine the presence or concentration of said substance. The path length of the excitation light through the test solution in Morris is typically 8 mm. Morris does not describe test devices for performing the method described therein which enable the detection of substances in very small sample volumes.

It is desirable to minimize the amount of sample that is necessary for performing the assay. For example, a limited supply of sample may be available for testing, e.g., on neonates. In addition, small samples require fewer reagents, reducing the costs associated therewith. However, the sensitivity of the assay may be compromised when using very small sample sizes. Thus, it would be desirable to have a device that enables use of very small sample sizes, but which does not sacrifice assay sensitivity.

Furthermore, diagnostic assays typically require the mixing of the sample of interest with the components of the reagent systems prior to performing the assay. This may require the reagents to be prepared before running the assay. If the reagents have a short shelf life, the reagent may have to be prepared frequently, which may be costly and which may introduce additional errors into the system. Similarly, having to prepare reagents decreases the time efficiency of the assay. It would therefore be desirable to have a device which contains some or all of the reagents for the assay and which can be used in an automated system for performing diagnostic assays. Such devices would increase the time and cost efficiency of diagnostic assays.

SUMMARY OF THE INVENTION

The present invention relates to a device for detection of an analyte of interest that has excellent sensitivity, requires minimal sample volume and enables the use of an instrument that detects fluorescence to detect and measure changes in the absorption and light scattering properties of reaction media. The device of the present invention extends the scope of the fluorometric instrument to calorimetric and turbidimetric assays, and eliminates costly modifications of the instrument.

The diagnostic assay device of the present invention comprises a fluorophore element comprising a fluorophore embedded or isolated therein, and a reagent element, said fluorophore element and said reagent element having opposed surfaces which are spaced apart throughout a liquid transport zone a distance effective to cause capillary flow of a sample liquid introduced therebetween throughout the liquid transport zone, said opposed surface of said fluorophore element carrying a plurality of projections arranged throughout said surface in the liquid transport zone, each said projection being spaced apart from the others in a predetermined pattern and being in contact or virtual contact with said opposed surface of said reagent element. The projections function to control the flow of liquid between the opposed surfaces in the liquid flow zone. In a preferred embodiment the projections carried by the surface of the fluorophore element are arranged in an ordered pattern of parallel spaced rows and columns which extend along both dimensions of the plane of the surface to provide a liquid flow which is substantially uniform in the liquid flow zone. The device also includes an opening, such as an aperture extending through the fluorophore element, to permit a liquid to be introduced into the liquid flow zone.

As aforesaid, the fluorophore element comprises at least one type of fluorophore embedded or isolated in the material that is used to make the assay device. For example, the fluorophore element is preferably made of flexible transparent plastic, e.g., polystyrene or polyester. The fluorophore can be selected from any fluorophore that can be embedded in an inert solid material, as is known in the art and based upon the teachings contained herein. A preferred fluorophore comprises rhodamine-B.

In one preferred embodiment of the present invention, the reagent element comprises at least one reagent layer carried by a support. Preferably, the reagent layer comprises at least one reagent of a diagnostic assay reagent system. The support is preferably transparent to wavelengths of radiation which are utilized to obtain a signal which is a function of an analyte in a liquid sample. Preferably, the reagent element comprises a thin film reagent element. The sample is added to the assay device, the liquid sample interacts with the reagents in the reagent element and the reaction takes place in situ. The combination of sample and reagents hereafter is referred to as the "reaction medium". The measurement is then taken at a certain time point(s) after the reaction has been initiated.

The controlled liquid flow characteristics of the device are particularly well suited for use with thin reagent elements because the volume delivered to the device is very small and controlled very precisely. Thus, the device of the present invention enables the uniform distribution of a small volume of precisely metered sample fluid on the surface of the reagent element. A further advantage is that evaporation of the sample fluid is minimized by reducing exposure of the sample to the ambient environment after being delivered to the diagnostic test element. Thus, changes in the analyte concentration is prevented or minimized.

The devices of the present invention enable the detection and/or quantification of analytes in very small sample volumes, e.g., within the range of from about 5 to about 20 $\mu$l, preferably, the range of from about 7 to about 10 $\mu$l. The projections on the fluorophore element enable the devices to be self-metering, by eliminating the need to pipette an exact amount of sample into the device. While a minimum volume may be necessary, the structure of the devices prevent more sample from entering the device than is necessary for performing the assay. The structure of the device therefore reduces variability in sample size. Furthermore, the use of the reagent element enables the concentration of reagents used in the assay to be controlled. Thus, the structure of the devices of the present invention increases the sensitivity and reproducibility of assays performed using the devices by reducing variability in sample size and reagent concentration.

In preferred assay devices, the projections are from about 50 to about 150 microns in height.

Liquid is introduced into the liquid flow zone, e.g., by pipette, through the aperture in the fluorophore element. The projections on the opposed surface of the fluorophore element serve to provide a controlled flow of the liquid in the liquid flow zone. It is necessary that the liquid contact the opposed surface of the reagent element in order for the liquid flow to begin. This condition can be ensured by various techniques which are described in detail in U.S. Pat. No. 5,051,237, incorporated herein by reference.

The fluorescent element of the device of the present invention provides a fixed concentration of fluorescent moieties, i.e., fluorophores, to generate the fluorescence response. When the reaction medium is placed in the pathway of the excitation beam, the intensity of fluorescence of the fluorophore depends on the intensity of the excitation light that reaches the fluorescent source. Thus, changes in the light absorptive properties of the reaction medium, due to changes in analyte concentrations, cause changes in the intensity of the light impacting the fluorescent medium. In addition, the amount of fluorescence emitted by the fluorophore and detected is further attenuated by the absorptive or scattering properties of the reaction medium.

In use, the excitation light is generated by a light source and passes through the sample toward the fluorescence source. The amount of excitation light that reaches the fluorescent source depends on the absorptive or scattering properties of the reaction medium. That is, the greater the absorptive, or scattering properties of the medium, the less light will reach the fluorophore compartment. The amount of fluorescent light produced by the fluorescent source depends on the amount of excitation light that reaches the source. Thus, the amount of fluorescent light produced is related to the amount of light absorbed or scattered by the reaction medium. The amount of light that is absorbed or scattered will depend on the presence of or amount of analyte in the sample, depending on the type of assay reagent system being used.

The amount of fluorescent light generated is measured by a detector in the fluorometer. The amount of fluorescence may be measured from either side of the assay device. Additional attenuation is achieved when the fluorescent detector is placed on the same side of the device as the source of the excitation light. The emitted fluorescence passes again through the reaction medium to the detector and, if the reaction medium also absorbs light at the fluorescence wavelength, the light is again attenuated.

To relate the fluorescent intensity to the concentration of the analyte in the sample of the reaction medium, the fluorescence emitted from the medium is compared to a standard, or a set of standards, having known concentrations of analyte. Such standards are known in the art. The accuracy of the assay can be improved by measuring the fluorescence before and after the chromogenic or turbidimetric reaction takes place and subtracting the intensities to obtain the net value of the change caused by the reaction. The assay may also comprise measuring the amount of fluorescence before initiation of the reaction and comparing the two values.

The assay devices of the present invention can be modified for use on any instrument capable of measuring and/or detecting fluorescence. One preferred instrument is the OPUS® Immunoassay System manufactured by Dade Behring Inc.

DETAILED DESCRIPTION OF THE INVENTION

Figure 1:
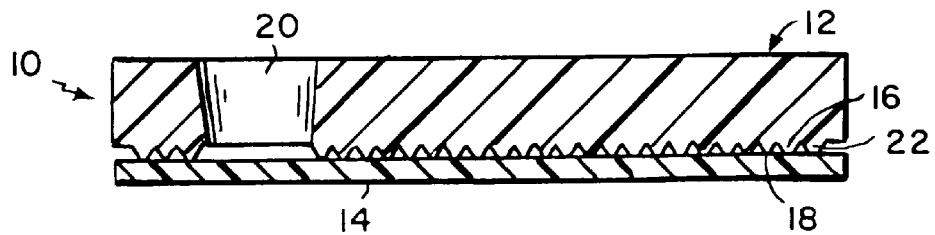
FIG. 1 is a partially schematic cross-sectional view of a liquid transport device according to the invention.

The present invention relates to the use of a diagnostic assay device for detection of an analyte of interest that has excellent sensitivity, requires minimal sample volume and enables the use of an instrument that detects fluorescence to detect and measure changes in the absorption and light scattering properties of reaction media. The diagnostic assay device of the present invention maintains a constant concentration of fluorophores and enables the measurement of changes in the amount of light emitted from the fluorophore depending upon the properties of a sample that is placed in the pathway between the fluorophore and the excitation light. For example, the amount of excitation light that reaches the fluorophore will depend on the light aborptive or light scattering properties of the reaction medium. In addition, the intensity of the fluorescence of the fluorophore is altered by changes in the absorptive or scattering properties of the medium. See FIG. 2.

The term "transmittive properties" as used herein refers to the amount of light that passes through an assay solution within a particular wavelength band when a beam of light of known intensity is passed through the assay solution and generally depends upon the absorption or turbidity of the assay solution. The term "change in the transmittive properties" refers to the change in the amount of light absorbed or scattered by the assay solution within a particular wavelength band wherein the change results substantially from the interaction of the analyte and a reagent system specific for the analyte. The change in the transmittive properties, that is, the change in the amount of light absorbed or scattered by the assay solution within a particular wavelength band is proportional to the concentration of the analyte in the assay solution.

The term "analyte" as used herein refers to a substance that is quantified or detected by an experiment procedure and includes any substance which is capable of being colorimetrically or turbidimetrically determined. That is, the analyte must be capable of producing a detectable change in the transmittive properties of the reaction medium related to the concentration of the analyte in the reaction medium. Examples of analytes include, but are not limited to, small molecules and antigens. Representative analytes that may be assayed in accordance with the present invention include, for example, glucose, uric acid, cholesterol, creatinine, lactate, lactate dehydrogenase (LDH), triglycerides, immunoglobulins, cholinesterase, serum glutamate oxalactate transaminase (SGOT), serum glutamate pyruvate transaminase (SGPT), creatine phosphokinase (CPK), ethanol, total protein, albumin, calcium, bilirubin, blood urea nitrogen (BUN), ammonia, magnesium, phosphorous, chloride and the like.

The present invention is also useful for detecting and measuring low amounts of substances in samples other than biological fluids. For example, this assay is useful in detecting and determining low levels of contaminants in environmental samples of soil, water and food products. The following is a partial list of examples of herbicides, pesticides and other contaminants for which this assay would be useful: Atrazine, Chlordane, Chlomeb (and other chlorinated pesticides), DDT, Demeton, Diazinon (and other organophosphorous pesticides), Diethylphthalate (and other phthalate esters), Dimethoate, Dimethylphthalate, Dimethoate, Etridiazole, Hexachlorobenzene, Malathione, Methyl parathion, Molinate, Naphthalone, Phorate, Propachlor, Simazine, Triflurilin and 2,4-D (and other Phenoxyacid herbicides).

The above lists are meant to be exemplary and are not intended to limit the scope of the present invention.

The term "sample suspected of containing the analyte" refers to any sample which is reasonably suspected of containing the analyte of interest. The sample is typically an aqueous solution such as a body fluid from a host, for example, urine, whole blood, plasma, serum, saliva, semen, stool, sputum, cerebral spinal fluid, tears, mucus, or the like, but preferably is plasma or serum. Or as described above, the sample can be samples of water, soil or food products. The sample can be pretreated and can be prepared in any convenient medium which does not interfere with the assay. An aqueous medium is preferred.

The term "fluorometer" refers to an instrument designed to measure fluorescence, typically comprising a light source, filters and detectors. Fluorometers are known in the art. A preferred fluorometer is the OPUS® Immunoassay System, Dade Behring Inc., which is an instrument for the continuous access automated immunoassay of analytes. The operation of the OPUS® Immunoassay System is described in Olive, C., "P. B. Diagnostics' OPUS® Immunoassay System," *Journal of Clinical Immunoassay*, Vol. 14, No. 2, 1991, p. 126–132, the entirety of which is incorporated herein by reference.

The term "fluorophore" or "fluoresce" refers to a compound having a fluorescent moiety. A wide variety of fluorophores may be used in the assay device of the present invention. Representative classes of fluorophores that may be employed in the present invention include for example fluoresceins, rhodamines, flavins, coumarins, napththalenes, acridines, anthracenes, polynuclear fused hydrocarbons, stilbenes, anthranilic acids, aminostyrylpyridines, quinolines, salicylic acids, cyanines, oxonols, phenanthidines, fluorescamines, as well as derivatives and salts thereof Illustrative of specific fluorophores that may be employed include, for example, eosin, rhodamine, aminonaphthalene sulfonate, acriflavin, fluorescein, dihydroxybenzoic acid, hydroxyquinoline, NADH, riboflavin, brilliant sulfaflavin, quinine, naphtholsulfonic acid, thioflavin, coumarin, acridine orange, 8-anilino-1-naphthalene sulfonic acid, oxazine, umbelliferone, acridine, resorufin, and derivatives and salts thereof. One of ordinary skill in the art can readily select appropriate fluorophores for use in the present invention based upon the teachings contained herein.

The term "effective amount of a fluorophore" as used herein, refers to a concentration of fluorophore sufficient to produce a detectable signal. Such effective amounts are generally ascertained by one of ordinary skill in the art and depend upon one or more factors such as for example, the specific fluorophore, the material used for making the diagnostic assay device, and/or the instrumentation utilized to measure the intensity of the fluorescence.

The term "reaction medium" as used herein refers to the test solution that is placed in the pathway between the excitation light source and the fluorophore. It comprises the sample suspected of containing the analyte of interest, a known amount of an analyte, e.g. a control or calibrator, or no analyte, i.e., a blank. It also comprises components of a reagent system. The excitation light from the source impinges the assay device and passes through the reaction medium. By incorporating fluorescent dyes into the assay device, the fluorescence emitted from the assay device is attenuated by changes in the transmittive properties of the reaction medium in the liquid transport zone.

The term "reagent system" as used herein refers to a chemical system containing one or more reagents which in the presence of the analyte of interest produces a change in the transmittive properties of the reaction medium. Reagent systems effective in the methods of the present invention will depend on the specific analyte to be determined and whether the change in the transmittive properties of the reaction medium to be measured is due to the change in the color or turbidity of the reaction medium. In a colorimetric assay, that is, wherein the change in color of the assay solution is related to the change in the transmittive properties of the reaction medium, a chromogenic reagent system is employed. In a turbidimetric assay wherein the turbidity, that is, the amount of light blocked or scattered by a suspension of particles, is related to the change in the transmittive properties of the assay solution, a turbidimetric reagent system is employed.

The term "chromogenic reagent system" as used herein, refers to a chemical system containing one or more reagents which will react in accordance with a specific reaction sequence with the analyte to be determined to produce a detectable change in the transmittive properties. For the purposes of the present invention, the various reagents comprising such chromogenic reagent systems may be added individually or in any combination to the assay solution, unless the order of addition is limited by the particular reaction sequence. The chromogenic reagent systems utilized for calorimetrically determining ligands are well known in the art. Various assay kits and reagent systems are commercially available and employ standard techniques and reagents. In general, those calorimetric procedures rely on the principle that an analyte will react with a chromogenic reagent system containing a color-producing reagent, to produce a detectable color change in the assay solution. Representative chromogenic reagent systems include for example, oxidase reaction systems, including end point and kinetic determinations, and NADH/NAD reaction systems. For example, an oxidase reaction system utilized oxidative enzymes to react with the analyte to release hydrogen peroxide which subsequently reacts with a dye in the presence of peroxidase to produce a change in the calorimetric properties of the assay solution as an indication of the amount of analyte in the sample. An NADH/NAD reaction system relies upon the reduction of NAD to NADH or the oxidation to NADH to NAD and the subsequent reaction with a dye system to produce a change in the colorimetric properties of the assay solution as a measure of the concentration of analyte in the sample.

The term "turbidimetric reagent system" as used herein refers to an assay system containing one or more reagents that will interact with the analyte in the sample to produce a detectable change in the turbidity of the reaction medium. Turbidimetric reagent systems are well known in the art and the reagent systems employed in such assays are readily ascertained by one of ordinary skill in the art.

The term "effective amount of reagent system" as used herein, refers to an amount of reagent system sufficient in the presence of an analyte to produce a detectable change in the calorimetric or turbidimetric properties of the assay solution. Such effective amounts are readily ascertained by one of ordinary skill in the art.

FIG. 1 shows a preferred embodiment of a liquid transport device according to the invention. It should be noted that the thickness of the device has been magnified for ease of illustration; the actual preferred devices of the invention are relatively thin, having a typical thickness in the range of from about 2 to about 10 mm. The device 10 includes a fluorophore element 12 and a reagent element 14 having opposed surfaces 16 and 18 respectively. The fluorophore element 12 includes an aperture 20 which is in fluid communication with the liquid flow zone defined by opposing surfaces 16 and 18 to allow a sample fluid to be introduced thereinto. Surface 16 of the fluorophore element 12 carries a plurality of projections 22 which provide a controlled flow of the fluid throughout the liquid flow zone. The projections 22 may be in contact with surface 18 as shown in FIG. 1 or in virtual contact, that is, spaced slightly apart from the surface. The distance between opposing surfaces 16 and 18 is generally in the order of from about 50 to about 150 microns or more. The height of projections 22 is generally in the range of from about 50 to about 150 microns or more and the preferred height is from about 80 to about 120 microns. The appropriate thickness of the fluorophore element can readily be determined by one of ordinary skill in the art. Preferably, it is between about 0.5 mm to about 5 mm thick, but most preferably about 1–2 mm.

The fluorophore element 12 may be transparent or opaque and may be made from any suitable material including synthetic, film-forming polymeric materials such as, for example, polyvinylacetate, polyvinylchloride, polyvinylchloride-polyvinylalcohol copolymers, polypropylene, polystyrene, cellulose acetate butyrate, hydrolyzed cellulose acetate butyrate, styrene acrylonitrile and the like, metals, ceramics, etc. Preferably the material does not substantially interfere with the functioning of the fluorophore contained therein. The fluorescence of the modules may be adjusted by using different ratios of the fluorescent moieties to the non-emitting plastic material as long as it comports with the measuring capacity of fluorescent analyzer.

Fluorescent dye concentrates for polystyrene and polyester are known in the art. The fluorescent dye concentrates include the Lumogen® Dyes sold by BASF Corporation, such as, for example, yellow 038, orange 240, red 300, violet 570 and the like. Rhodamine is also commercially available. Any fluorescent dye compatible with a solid moldable plastic matrix may be employed. The fluorescent dye may be incorporated in the raw plastic material prior to molding by grinding, or by adding colorants to plastics, as is known in the art.

The surface 16 of the fluorophore element may be treated such as by hydrolysis or with an additive which causes its surface to be more easily wetted by the fluid. Proteins such as gelatins and albumins as well as surfactants are suitable for this purpose. Some metals and polymeric materials strongly absorb proteins and the contact angles of liquids applied thereto are changed significantly. Polystyrene and hydrolyzed cellulose acetate butyrate are preferred materials. The fluorophore element 12 including aperture 20 and projections 22 can be made by various techniques including injection molding.

It is preferred to arrange the projections 22 on surface 16 in parallel spaced rows and columns extending substantially along both dimensions of the plane of surface 16 as shown in U.S. Pat. No. 5,051,237. In another example, the projections are in the form of grooves on the surface 16. The spacing of the projections is dependent upon the type of liquid sample involved and the device application. In a preferred embodiment wherein the device is used for a diagnostic assay for a biological fluid, e.g., plasma or serum, the device is typically rectangular, with typical dimensions of about 7 by 10 mm in width and length, respectively. It has been found to be preferred in this embodiment to arrange the projections 22 apart in the range of from about 0.25 mm to about 0.4 mm on centers. It has been found that excellent spreading of plasma or serum samples can be obtained in a rectangular 7×10 mm device with 25 columns along the longer dimension and 37 rows along the shorter dimension.

The projections 22 may be various shapes such as convex, trapezoidal or v-shaped. The choice of the shape in any particular instance is dependent in part upon the device application. For example, in a biological diagnostic assay device it is desirable to have as little as possible of the surface of the reagent element covered by contact with the projections so that a uniform concentration of the sample fluid can be applied across the element. Thus, in assay devices where the projections are used to define the gap it is preferred to use v-shaped projections or conical projections with a very slightly rounded tip.

The aperture 20 may be of any size and configuration. The aperture may be large enough to permit the fluid sample, which may be a droplet having a very small volume, e.g., of about 8 to 10 $\mu$l, to contact surface 18 without touching the sides of the aperture. Of course the volume of the sample depends on the type of liquid involved, e.g., aqueous or non-aqueous, and the device application. However, in preferred embodiments the aperture is as small as possible to minimize evaporation of the liquid sample. The shape of aperture 20 may be circular with the same diameter throughout or, as shown in FIG. 1, the diameter may become progressively smaller from the top to the bottom surfaces of member 12. It is preferred, as illustrated in FIG. 1 to have the aperture 20 off-centered since it has been found that more uniform spreading of the liquid in the liquid flow zone can be obtained in this manner.

A capillary break 24 (see FIG. 4) may be disposed in the devices according to the invention. The capillary break assists in confining the sample liquid to the liquid flow zone defined by projections 22. As noted previously, in the case of diagnostic assay devices it is desirable to have an aperture 20 which is as small as possible in order to minimize any evaporation of the sample fluid during the assay procedure. For 8–10 $\mu$l samples of plasma or serum it has been found that an aperture diameter of about 2 mm is satisfactory to minimize undesired evaporation of the sample.

The devices of the present invention enable the detection and/or quantification of analytes in very small sample volumes. Preferably, the volume of sample added to the device is within the range of from about 5 $\mu$l to about 20 $\mu$l. More preferably, the volume is within the range of from about 7 $\mu$l to about 10 $\mu$l. As aforesaid, the projections on the fluorophore element enable the devices to be self-metering. That is, the projections eliminate the need to pipette an exact amount of sample into the device. While a minimum volume may be necessary, the structure of the devices prevent more sample from entering the device than is necessary for performing the assay. The structure of the device reduces variability in sample size. Furthermore, the amount of reagents used in the assay are also kept consistent by the use of the reagent element. Thus, the structure of the device increases the sensitivity of the assay by reducing variability in sample size and reagent concentrations.

In the diagnostic assay devices of the invention the reagent element 14 may be made of a single layer or multilayers of reagents. A typical reagent layer has a thickness of about 0.001 to 0.01 mm and comprises one or more layers residing on a support layer which is transparent. The reagent layer(s) comprise an effective amount of at least one reagent of a chromogenic or turbidimetric reagent system and can be readily selected from reagent systems known in the art. The reagent layer may include various other layers as are known in the art including, for example, a registration layer for holding a signal generating species formed in, or released from, another layer, etc. The layers preferably do not act as an optical screen. One of ordinary skill in the art can readily select and prepare a reagent element based upon the teachings contained herein.

Figure 3A:
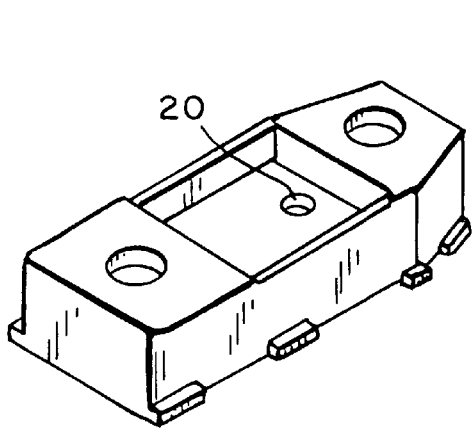
FIG. 3 is a drawing showing one embodiment of a device of the present invention.
Figure 3B:
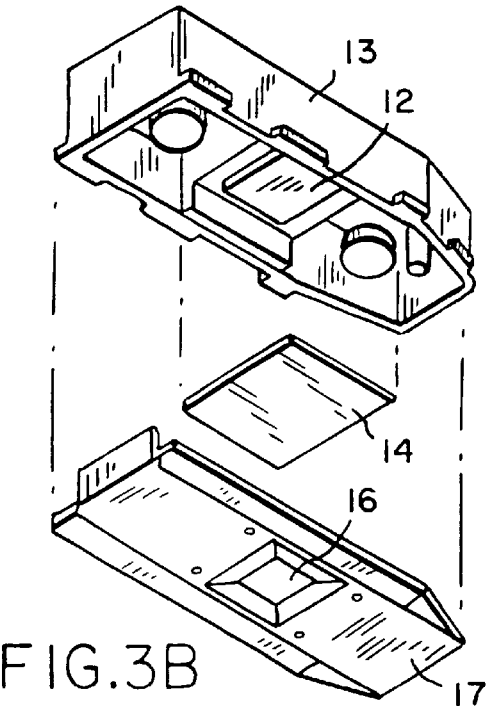

FIG. 3 illustrates an embodiment of the present invention having a reagent element 14 comprising a reagent layer incorporated in an assay device. The assay element 14 reagent layer may include reagent components bound to the surface of a support layer or to a matrix material or by being physically held by the matrix material. The matrix material may be a nonporous hydrophilic gel material such as gelatin, a polysaccharide, a derivatized polysaccharide, including mixtures thereof, or the like. Optional layers may comprise an antiabrasion layer of a material such as a polysaccharide. The reagent element in this embodiment is in the form of a chip that can be manufactured separately from the assay device and inserted during assembly.

In practice, the fluid sample is introduced into the aperture 20 of the first member and is spread uniformly across the surface of the reagent element by the projections 22. Accordingly, a uniform concentration of any analyte present in the sample is distributed across the reagent element and the liquid fills the liquid flow zone. The liquid dissolves the reagent(s) present in the reagent layers on the reagent element uniformly and the chromogenic or turbidimetric reaction occurs.

Figure 4:
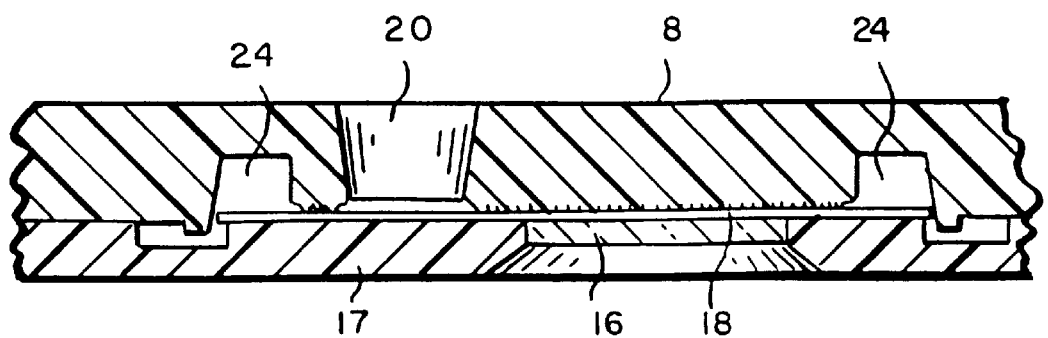
FIG. 4 is a partially schematic, cross-sectional view of a device of the present invention.

FIG. 4 illustrates an embodiment of an assay device wherein the reagent element 18 is held in a flat position by means of bottom member 17 which may be made of a polymeric film-forming material. Bottom member 17, which may be transparent or opaque, includes a transparent window area 16 through which the signal developed in the reagent element can be read out by the optical system.

The wavelength of light absorbed or scattered by reaction of the analyte with the reagent system preferably overlaps with the wavelength used for the excitation light of the fluorophore. The reagent system and fluorophore are selected so that the transmittive change in the reaction medium will cause a change in the fluorescence of the fluorophore that can be measured by the detector. To maximize the sensitivity of the assay, preferably both the ranges of the excitation light and the wavelength range of the fluorescing light falls within the range of light absorbed or scattered by the reaction medium. The fluorophore art is well-developed. One of ordinary skill in the art can readily select an appropriate fluorophore based on the detector or analyzer used. For example, in assays that utilize the OPUS® Analyzer, a fluorophore is used that has been optimized for that instrument, e.g. rhodamine-B. The selection of a fluorophore for use in the test module of the present invention can readily be accomplished by one of ordinary skill in the art, based upon the teachings herein.

Although the concentration of analyte which may be determined in accordance with the methods of the present invention depends in a large part upon the specific fluorometer employed and the specific reagent system utilized, samples containing analytes in a concentration range as low as 0.001–0.1 mM can be determined using the device of the present invention.

Various ancillary materials may be employed in the methods in accordance with the present invention. For example, buffers will normally be present in the reaction medium, as well as stabilizers for the reaction medium and the assay components. Frequently, in addition to these additives, proteins may be included, such as albumins, organic solvents such as formamide, quaternary ammonium salts, polycations such as dextran sulfate, or surfactants, particularly non-ionic surfactants, binding enhancers, e.g., polyalkylene glycols, or the like.

The invention is more fully described by reference to the Figures and the following description.

Figure 2:
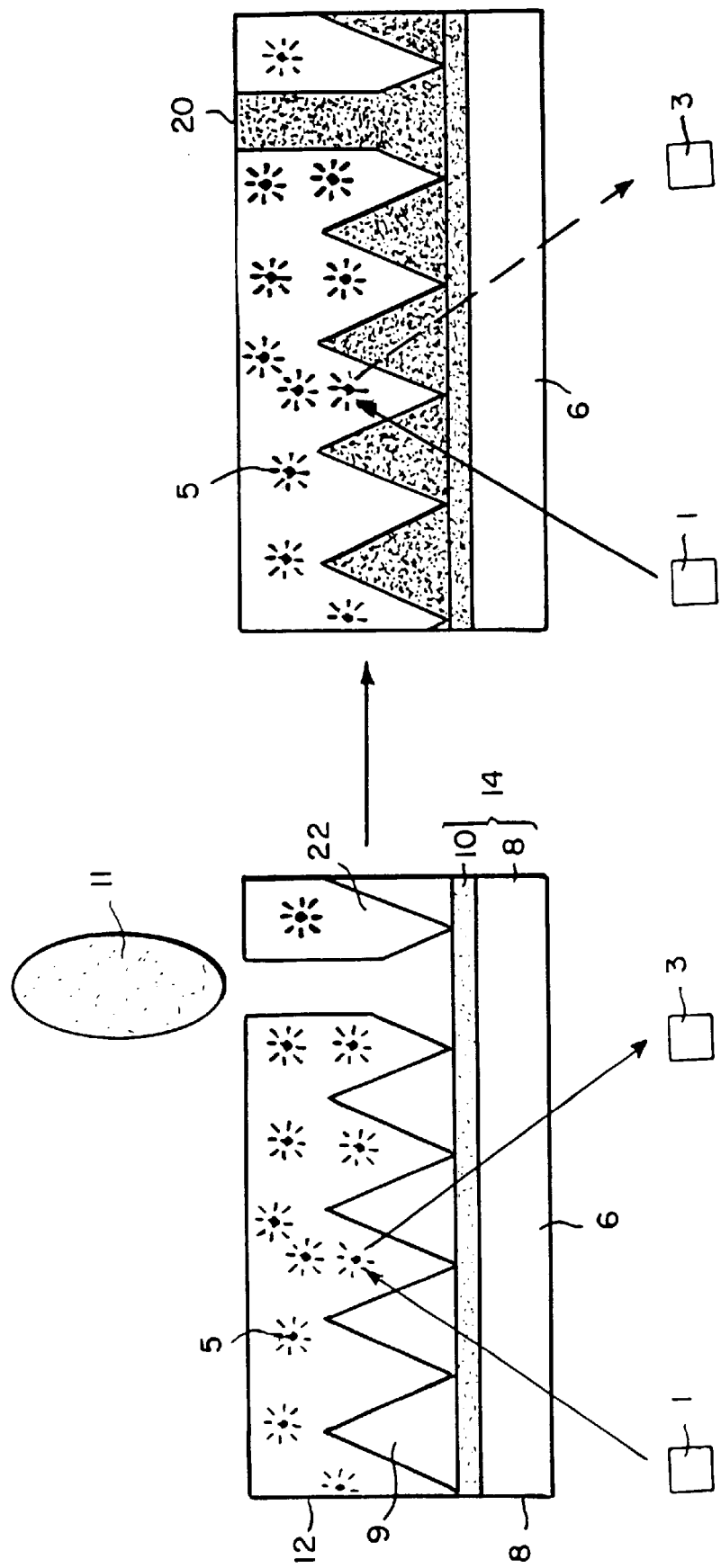
FIG. 2 is a drawing illustrating diagrammatically the practice of the invention wherein the reaction takes place within a device of the present invention.

The principle of the present invention is diagrammatically illustrated in FIG. 2. In this embodiment, the fluorophore element 12 comprises a fluorescent dye 5 embedded in material, e.g., plastic. The fluorophore element has projections 22 which extend into the liquid transport zone and which function as a metering device, assuring precise volume pipetting.

The reagent element 14 in this embodiment comprises a reagent layer 10 in which some or all of the reagents required for the assay are provided and a transparent support layer 8. The reagents may be coated onto the support either directly or in clear layers 10 of agarose, gelatin or the like. The number of layers may vary, each having different reagents, as needed. The layers preferably do not act as an optical screen. The sample suspected of containing the analyte 11 is pipetted into the assay device through opening 20. The sample reacts with the reagents in the reagent layer to provide a change in the transmittive properties of the reaction mixture.

The amount of excitation light that reaches the fluorophore is attenuated by the light transmittive properties of the reaction medium 9 which is in the pathway of the excitation light. The intensity of fluorescence is measured by a detector 3. For example, if a colorimetric assay is used, the reaction medium 9 will absorb light, i.e., produce a certain color, in proportion to the amount of analyte in the sample in the reaction medium. The more analyte present in the sample, the more or less light is absorbed by the reaction medium. In assays in which absorbance is proportional to the amount of analyte present, the more analyte that is present, the more light is absorbed. As more light is absorbed by the reaction medium, less light reaches the fixed fluorescent source 9. Thus, the more analyte in the sample, the less fluorescence produced by the fluorescent source. In the embodiment shown, the light emitted by the fluorophore, i.e., the fluorescence, travels back through the reaction medium to detector 3. The difference in fluorescence transmission is measured by the detector 3.

Detector 3 can be positioned on the same side of the reaction medium (shown in FIG. 2) or alternatively, on the other side of the fluorescent source (not shown). In FIG. 2, the intensity of fluorescence is attenuated by the reaction medium 9 before reaching detector 3. In certain embodiments, the detector is positioned on the other side of the fluorophore source. In such an embodiment, only the intensity of the excitation light is attenuated.

In certain embodiments that utilize turbidimetric assays, the reaction medium will scatter the excitation light 1 before it reaches the fluorescent source. The amount of light scattered depends on the presence of, or the amount of, analyte present in the sample added to the reaction medium. The more analyte in the reaction medium, the greater the amount of light scattering. As more light is scattered, less light reaches the fixed fluorescent source. The more analyte in the sample, the less fluorescence produced by the fluorescent source. Thus, the degree of fluorescence is inversely proportional to the amount of analyte in the solution.

In assays in which the degree of absorbance or light scattering is inversely proportional to the amount of analyte present, the amount of fluorescence will be directly proportional to the amount of analyte present.

As described above, calorimetric, and turbidimetric assays are known in the art. The appropriate assay for the analyte of interest can readily be selected by one of ordinary skill in the art based upon teachings disclosed herein.

In some embodiments it may be desirable to have only some of the reagents incorporated into the reagent element. In such embodiments, the other reagents and/or additional components, such as buffers, can be added to the sample prior to placement in the diagnostic assay device.

The diagnostic assay devices of the present invention keep the fluorescent source separated from the reaction medium. As a result, there is no reaction, either chemical or immunological, between the fluorescent source and any other component of the assay system. The present invention therefore avoids any interference from the fluorophore. In addition, it is known that dyes, e.g. fluorophores, imbedded in a solid phase are more stable than in solution. Thus, the fluorescent source will degrade slower, resulting in a more economical test.

FIG. 3 shows one embodiment of a assay device of the present invention in assembled (a) and unassembled (b) form. This device comprises a top portion 13 that has the fluorophore element 12 and a bottom member 17 which as a transparent window 16. A reagent element 14, as described above comprising a reagent layer is sandwiched between the fluorophore element and the bottom element. The fluorophore element has an opening 20 which allows the sample to be added to the device. This is shown in FIG. 3a. In use, excitation light enters the device through window 16 and the amount of fluorescence emitted is detected by the instrument, also through window 16.

In these embodiments of the invention, the module is specific to the particular analyte in the biological sample of interest, which increases the versatility of the assay by using reagents specifically designed for the assay or commercially available assays.

In certain embodiments of the present invention, the presence of, or amount of, more than one analyte can be determined. Such embodiments utilize more than one fluorophore, one for each of the analyte to be detected. Each fluorophore preferably has a narrow and separate range of excitation light and fluorescence. The reagent system for each of the analytes must be selected so that the analytes absorb or scatter the light at different wavelengths, within one of the ranges for one of the fluorophores. In such an embodiment, the instrument preferably can generate and detect the different wavelengths.

The assay device and its parts can be made by various techniques known in the art including injection molding.

The parts of the assay device can be manufactured separately, i.e., the fluorophore element and the reagent element, and assembled to form the complete device. In these cases, the reagent layer can easily be applied to the reagent element and assembled with the fluorophore element, as shown for example in FIG. 3. Alternatively, the device can be assembled in one piece and the reagents applied in liquid form into the liquid transport zone through the opening in the fluorophore element, prior to performing the assay. The reagents may be allowed to dry, if desired, to form a film coating the inside of the device.

The devices of the present invention can be used to make qualitative and/or quantitative determinations. That is, the results can provide a yes/no, response, e.g., if there is any change in the transmittive properties of the reaction medium, the analyte is present in the sample. Alternatively, the devices can be used to precisely determine the amount of analyte in the sample. Such a determination will depend on limitation of the system, e.g., the sensitivity of the fluorometer used.

In commercial use the diagnostic assay device of the invention preferably is used with an automated test apparatus which performs the analysis automatically and records the result. In such test apparatus the diagnostic assay device is typically mounted in a holder which could be an integral part of the apparatus. Where the assay device is of a flat planar configuration and it is used in an automated test apparatus it will be appreciated that the area of the device which is read should be a fixed distance from the optical readout system. This condition can be ensured by various techniques. FIG. 4 illustrates an embodiment of an assay device wherein the assay element 18 is held in a flat position by means of bottom member 17 which may be made of a polymeric film-forming material. Bottom member 17, which may be transparent or opaque, includes a transparent window area 16 through which the signal developed in the assay element can be read out by the optical system.

The tests performed on the OPUS® instrument involve the measurement of changes of the transmittive properties of the reaction medium at the wavelength corresponding to one of the two channels of the instrument (580 um and 450 um). The tests may be chromogenic such as chemistries, homogeneous chromogenic immunoassays, or colormetric latex agglutination tests, and commercially available tests such as hemagglutination for ABO typing.

The results of measurements of the same sample in different assay devices are reproducible since the test does not require that all devices have exactly the same concentration of fluorescent dye. Differences between devices can be normalized because the fluorescence of the device can be read prior to the reaction and the net change caused in the fluorescence by the reagents can be measured. Another aspect of the present invention is a kit for detecting the presence of or determining the amount of analyte in a fluid sample.

Appropriate reaction conditions are chosen for using the devices in accordance with the present invention. The following description sets forth suitable conditions, which are subject to modification by those skilled in the art depending on the specific reagents and assay protocol chosen for any particular application.

The following is a non-limiting example of the devices of the invention. The following example is provided to more clearly illustrate the aspects of the invention and is not intended to limit the scope of the invention. The example is merely illustrative of the how the device of this invention can be used for determining the presence or amount of analyte in a sample.

EXAMPLE:

Ethanol Assay

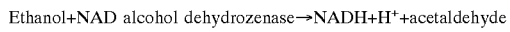
Ethanol+NAD alcohol dehydrozenase→NADH+H⁺+acetaldehyde

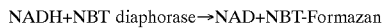
NADH+NBT diaphorase→NAD+NBT-Formazan

NAD=nicotinamide adenine dinucleotide
NADH=nicotinamide adenine dinucleotide, reduced form
NBT=p-nitro blue tetrazolium chloride
Materials and Reagents:
1. Ethanol Serum Calibrators
   0, 25, 50, 200, 300 mg/dl
   Ethyl Alcohol—200 Proof Dehydrated Alcohol, U.S.P. (Quantum Chemical Corporation, USI Division)
   0.22 µm filtered, in processed human serum that contains preserving agents and buffering materials, including Kathon (150 ppm activity), Aprotinin (15 KIU/ml), and HEPES (witterionic buffer, 10 mM pH 7.5).
2. Ethanol Reagent Element
   a) A support layer was coated with a mixture of reagents in gelatin gel with the following proportions:
   6000 mg/m² gelatin (Knox)
   5000 mg/m² trehalose (Sigma-Aldrich Co.)
   2500 mg/M² Tris pH 8.5 (Sigma-Aldrich Co.)
   1750 mg/m² Bovine Serum Albumin (Sigma-Aldrich Co.)
   20 mg/M² triton-X100 (Sigma-Aldrich Co.)
   3 mg/M² alcohol dehydrogenase (Boehringer Mannheim)
   0.803 mg/M² diaphorase (Boehringer Mannheim)
   b) Assay Buffer
   1.8 mM p-nitro blue tetrazolium chloride (NBT) (Research Organics Co.)
   1.8 mM B-Nicotinamide-adenine dinucleotide (NAD) (Boehringer Mannheim)
   50 mM sodium citrate pH 6.7 (Sigma-Aldrich Co.)
Protocol:

Enzymatic degradation of ethanol results in eventual formation of a formazan dye that absorbs light within the wavelength used for fluorescent excitation in the OPUS® analyzer.

A reagent element having a portion of the reagents necessary for the assay was prepared by coating a layer of plastic with the reagent described above. Another portion of the reagents was mixed externally with the sample. The reagent element consisted of a single gelatin layer containing the reagents coated in a film on a plastic base. The film coating contained alcohol dehydrogenase and diaphorase along with the buffer components, surfactants, and reagents necessary to stabilize the enzymes. The film was enclosed in a plastic assay device having molded projections for sample spreading.

The assay device had an inherent fluorescence associated with the fluorescent dye, rhodamine, embedded in the plastic.

Each patient sample (10 µl) was first mixed with a reagent containing NAD and NBT in a buffer, manually or by the automated OPUS® instrument using its automated pipetting system. After mixing, 10 µl of the mixture was applied to the assay device containing the remainder of the assay reagents coated on the reagent element in the assay device.

The fluorescent signal of the assay device was determined prior to reaction with the reagents, and after the reaction was complete (6 minute incubation at 37° C.). The formation of the NBT-formazan dye interfered with the fluorescence of the rhodamine in the fluorophore compartment in the assay device so that the generated signal was inversely proportional to the ethanol concentration in the sample. The signal was converted to dose (mg/dl ethanol) using a standard curve fluorescent stored in the memory of the analyzer. The results for 20 samples are shown in Table 1. "Dose" indicates the amount of ethanol present.

TABLE 1

|  | LOW | | MEDIUM | | HIGH | |
|---|---|---|---|---|---|---|
|  | Signal | Dose (ms/dl) | Signal | Dose (ms/dl) | Signal | Dose (ms/dl) |
| Mean | 5.75 | 55.5 | 4.26 | 114 | 2.82 | 271 |
| Standard deviation | 0.15 | 3.5 | 0.10 | 6 | 0.14 | 24 |
| Coefficient of Variation |  | 6.3% |  | 5.2% |  | 8.8% |

The results are reproducible within clinically acceptable standards.

The invention has been described in detail with particular reference to the preferred embodiments thereof. However, it will be appreciated that modifications and improvements within the spirit and teachings of the inventions may be made by those in the art upon considering the present disclosure.

What is claimed is:

1. A diagnostic assay device comprising (a) a fluorophore element comprising a fluorophore embedded or isolated therein, and (b) a reagent element, said fluorophore element and said reagent element having opposed surfaces which are spaced apart throughout a liquid transport zone a distance effective to cause capillary flow of a sample liquid introduced therebetween throughout the liquid transport zone, said opposed surface of said fluorophore element carrying a plurality of discrete noncontinuous projections arranged throughout said surface in the liquid transport zone, each said projection being spaced apart from the others in a predetermined pattern and being in contact or virtual contact with said opposed surface of said reagent element.

2. The diagnostic assay device as defined in claim 1 wherein said reagent element comprises at least one reagent layer carried by a support.

3. The diagnostic assay device as defined in claim 2 wherein said reagent layer comprises at least one reagent of a diagnostic assay reagent system.

4. The diagnostic assay device as defined in claim 2 wherein said support is transparent to wavelengths of radiation which are utilized to obtain a signal which is a function of an analyte in a liquid sample.

5. The diagnostic assay device as defined in claim 1 wherein the sample has a volume of from about 5 µl to about 20 µl.

6. The diagnostic assay device as defined in claim 1 wherein the sample has a volume of from about 7 µl to about 10 µl.

7. The diagnostic assay element as defined in claim 1 wherein said projections are from about 50 to about 150 microns in height.

8. The diagnostic assay device as defined in claim 1 further comprising means to permit introduction of a liquid between the opposed surfaces of said fluorophore element and said reagent element.

9. The diagnostic assay device as defined in claim 8 wherein said means to permit introduction of liquid comprises an aperture in said fluorophore element.

10. The diagnostic assay device as defined in claim 1, wherein the device comprises a transparent material.

11. The diagnostic assay device as defined in claim 10, wherein the transparent material comprises polystyrene or polyester.

12. The diagnostic assay device as defined in claim 1, wherein the fluorophore is selected from the group consisting of rhodamine.

13. The diagnostic assay device as defined in claim 1, wherein the concentration of analyte detected is from about 0.001 to about 0.1 mM.

* * * * *